United States Patent
Wheelock et al.

(10) Patent No.: US 11,624,853 B2
(45) Date of Patent: Apr. 11, 2023

(54) METHODS FOR PERFORMING FORMATION EVALUATION AND RELATED SYSTEMS

(71) Applicant: ExxonMobil Technology and Engineering Company, Annandale, NJ (US)

(72) Inventors: Brent D. Wheelock, Bloomsbury, NJ (US); Lang Feng, New York, NY (US); Qiuzi Li, Clinton, NJ (US); Harry W. Deckman, Clinton, NJ (US); Mehmet D. Ertas, Bethlehem, PA (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 180 days.

(21) Appl. No.: 17/158,318

(22) Filed: Jan. 26, 2021

(65) Prior Publication Data
US 2021/0239872 A1   Aug. 5, 2021

Related U.S. Application Data

(60) Provisional application No. 62/968,583, filed on Jan. 31, 2020, provisional application No. 63/024,195, filed on May 13, 2020.

(51) Int. Cl.
*G01V 3/20*   (2006.01)
*E21B 49/02*   (2006.01)
(Continued)

(52) U.S. Cl.
CPC ............. *G01V 3/20* (2013.01); *G01N 27/041* (2013.01); *G01N 33/24* (2013.01); *G06N 20/00* (2019.01); *E21B 49/02* (2013.01)

(58) Field of Classification Search
CPC ...... G01V 3/20; G01N 27/041; G01N 27/026; G01N 27/043; G01N 33/24; G06N 20/00;
(Continued)

(56) References Cited

U.S. PATENT DOCUMENTS 4,686,477 A   8/1987   Givens et al.
4,849,699 A   7/1989   Gill et al.

FOREIGN PATENT DOCUMENTS

CN   110703344 A    1/2020
WO   2002/50571 A2  6/2002
WO   2018/125214 A1 7/2018

OTHER PUBLICATIONS

Revil et al., Complex Conductivity Tensor of Anisotropic Hydrocarbon-Bearing Shales and Mudrocks, Nov.-Dec. 2013, Geophysics, vol. 78, No. 6, 16 pp. (Year: 2013).*

(Continued)

*Primary Examiner* — Toan M Le
(74) *Attorney, Agent, or Firm* — Vorys, Sater, Seymour and Pease LLP (57) ABSTRACT

Embodiments of an invention disclosed herein relate to methods for performing formation evaluation of a formation or formation's surrounding to identify and characterize the abundance and morphology of non-ionic conductor grains, "c-grains", within the formations that are evaluated by formation evaluation (FE) tools. The methods and related systems as disclosed herein are directed to correcting any existing FE logs that can be adversely affected by the presence of c-grains in the detection volume of FE tools, and/or obtaining new FE information that is unavailable by the application of existing FE methods.

22 Claims, 7 Drawing Sheets

(51) Int. Cl.
 *G01N 27/04* (2006.01)
 *G06N 20/00* (2019.01)
 *G01N 33/24* (2006.01)

(58) Field of Classification Search
 CPC ...... G06N 3/0454; G06N 3/088; G06N 3/045;
 E21B 49/02
 See application file for complete search history.

(56) References Cited

OTHER PUBLICATIONS

Zhi-Hua et al., "Resistivity dispersion in pyrite-bearing shaly sandstones", Applied Geophysics, vol. 16, No. 1, Mar. 2019, pp. 46-55.
Clavier et al., "Effect of Pyrite on Resistivity and Other Logging Measurements", Transactions of the SPWLA Seventeenth Annual Logging Symposium, Jun. 1976, pp. 1-34.
Holmes et al., "A Petrophysical Model to Quantify Pyrite Volumes and to Adjust Resistivity Response to Account for Pyrite Conductivity", 2013 AAPG ACE, May 2013, pp. 1-7.

\* cited by examiner

METHODS FOR PERFORMING FORMATION EVALUATION AND RELATED SYSTEMS

CROSS-REFERENCE TO RELATED APPLICATIONS

This application claims the benefit of priority from U.S. Provisional Application No. 62/968,583 filed Jan. 31, 2020, and U.S. Provisional Application No. 63/024,195 filed May 13, 2020, the entire contents of which are herein incorporated by reference in their entireties.

FIELD OF THE INVENTION

The invention relates to methods for performing formation evaluation of a formation or formation's surrounding. The methods may be applied in the area of hydrocarbon exploration, development, and production.

BACKGROUND OF THE INVENTION

Electrical resistance well logs are one of the key tools used in formation evaluation. Well logging tools employed by the industry use either galvanic or induction coupling to the formation and make measurements at two to four different frequencies. Methods to obtain broadband complex conductivity spectra are relatively well understood but not typically utilized. In industry, different service providers measure in different frequency ranges and the frequency at which resistance is measured can range from ~35 Hz (Laterolog) to ~1.1 GHz (EPT). Within a conductive medium, the tools probe their surroundings over an effective length L along the borehole, out to distances R that scale with the probe frequency f as the characteristic electromagnetic skin depth $\delta$:

$$R \sim \delta \sim \frac{1}{\sqrt{\sigma_0 \mu f}}.$$

In addition to probe frequency, the skin depth depends on the background conductivity $\sigma_0$ and magnetic permeability $\mu$ of the detection volume. For most situations of interest, the effective length L is dictated by the design of the tool and the magnetic permeability can be approximated by its value in vacuum, unless magnetic grains are present. Thus, the detection volume scales as:

$$V_d(f) \sim R^2 L \sim 1/(\sigma_0 f)$$

Therefore, in assessing formation resistance, the highest frequency measurement is typically used to assess resistance of fluids in the wellbore as well as that of the formation nearest to the wellbore. The lowest frequency measurement is used to assess resistance of the formation furthest from the wellbore. The measurements of resistance in the formation are then used in part of a work flow to assess lithology and presence of hydrocarbon. Methods to self-consistently extract formation conductivities are well established.

When non-ionically conducting mineral grains such as pyrite are present in the formation, it is known that there is an intrinsic frequency dependence to the resistivity. However, this is either not accounted for, or is removed by a calibration method that requires a core sample and assumes the entire formation behaves like the core. In formations such as shales where pyrite is routinely present, the resistivity tool becomes inaccurate because the pyrite changes the formation resistivity and adds a frequency dependence that is not properly accounted for. For example, it is often the case that when 3% pyrite is present the logging tool can be off by 50%.

Ideally one would like to assess the amount and type of pyrite or other sulfides present in a formation or a formation's surrounding, and remove its effect on the measurement of $\sigma_0$. A key benefit of this would be a significantly improved estimation of the resistivity of fluids, particularly hydrocarbons in the formation. At the present time, the resistivity log does not reliably provide a measure of "sweet spots" in logs of most unconventional resources.

Besides enabling a more accurate determination of the resistance of the formation, this would also benefit in more accurate geological interpretations for the depositional settings for the formation. Typically, pyrite found in shales that are prone to become an ultimate source of hydrocarbons is formed near the time when the organic matter in the shale was deposited on the mudline below a water column (ocean, inland lake, or river). The mudline can have an oxidizing or reducing environment, depending on prevailing conditions. High quality source rocks tend to deposit during episodes that cause the environment to be highly anoxic and reducing. The reason is that if oxygen is present, aerobic bacteria consume much of the deposited organic matter to produce $CO_2$, thereby reducing the hydrocarbon generating potential of the formation. Nevertheless, as the organic matter starts to get buried below the mudline, oxygen becomes transport-limited at some point, and in a region called the transition layer, aerobic bacteria can no longer sustain life, thereby allowing anaerobic sulfate-reducing bacteria to take over. The typical distance from the mudline to this transition layer, d*, varies, but under depositional conditions that favor high quality source rocks, has a typical range of:

$$d^* \sim 0\text{-}100 \text{ cm},$$

the lower limit corresponding to highly reducing situations where the mudline is already anaerobic, to a more oxygen-rich setting where there is a thin surface layer of aerobic activity. Other factors being equal, environments with smaller values of d* tend to produce shales with higher total organic carbon (TOC).

The deposition of non-ionically conducting sulfides like pyrite happens at this layer, as the dissolved sulfates in the water column diffuse down from the mudline, which allow sulfur-reducing bacteria to consume the organic matter left over from the aerobic processes above. Depending on the abundance of various cations in the pore fluid, a wide variety of mineral phases with different morphologies can form. When there is sufficient iron content, iron sulfides and pyrite can form. This initial formation of sulfide grains ceases once the pore fluids run out of sulfate ions, since sulfates are also transport-limited from the mudline, just like dissolved oxygen. Barring some diagenetic overprint, these sulfide grains can remain intact over geologic time.

The diagenetic overprint such as overgrowth or partial dissolution of these grains under conditions that chemically destabilize the minerals that they are made of can provide a wealth of information about the entire burial history of the formation. Therefore, a means to identify not only the abundance, but also the morphology of these grains can be a very powerful tool to understand the geologic history of a basin, and to provide leads on where to look for resource-rich areas. There is a vast literature full of such examples, but they all rely on recovery of a core from the subsurface and painstaking, detailed analysis by human experts. A method to retrieve this type of information through a formation evaluation tool can transform basin-scale exploration of source rocks and unconventional resources.

Since these grains typically have mass densities that far exceed the density of surrounding grains, (e.g., pyrite about 5.0 g/cc vs. clays/quartz about 2.6 g/cc) knowing their abundance also allows correction of logs that estimate the density of the rocks in the formation. Based on the example here, every 1% volume fraction of pyrite offsets the density by about 0.024 g/cc, which can cause misinterpretation of the mineralogy and/or porosity, if not accounted for correctly.

A recent article by Zhi-Hua Guo, Yan-Jie Song, Chao Wang and Xiao-Min Tang discusses the distortion of resistivity logs from pyrite (Applied Geophysics March 2019, Volume 16, Issue 1, pp 46-55). A summary of their conclusions is that "[[i]]n pyrite-bearing shaley sandstones, the distortion in the resistivity logging response of formations in high-frequency resistivity logging because of dispersion hinders the calculation of reservoir saturation." A much earlier paper looking at the effect of pyrite on resistivity and other logging measurements was published by C. Clavier, A. Heim, and C. Scala, (Schlumberger-Doll Research Center, Ridgefield, Conn.; Transactions of the SPWLA seventeenth annual logging symposium 1976).

There have been many attempts to provide approximate engineering solutions that adjust resistivity logs to account for pyrite. An example of a petrophysical model aimed at quantifying pyrite volumes and adjusting resistivity response accounting for pyrite conductivity was presented at the 2013 AAPG ACE in Pittsburgh Pa. (May 19-22) by Michael Holmes, Antony Holmes, and Dominic Holmes. Such models require some form of calibration with a core sample and will only be approximately valid. Often these approximate engineering solutions do not account for the frequency dependence of the pyrite signal.

In addition, there have been several attempts to modify borehole logging tools to be able to assess the effects of pyrite. U.S. Pat. No. 4,686,477 provides a description of one method to address this problem with multi-frequency excitation. This patent claims, among other things, a method for identifying complex lithologies of a rock formation comprising the steps of: (a) exciting at least a portion of said rock formation with a multi-frequency electric current, containing a plurality of frequencies such that all of said frequencies simultaneously excite said portion of said rock formation, (b) measuring the resulting voltage in said portion of said rock formation, (c) determining the phase and amplitude of the measured voltage at each of the plurality of simultaneous frequencies included in said multi-frequency electric current, (d) determining the resistivity of said portion of said rock sample at each plurality of simultaneous frequencies from the amplitude of said multi-frequency current at each of said plurality of simultaneous frequencies and said determinations of phase and amplitude for said measured voltage, (e) recording said resistivity and said phase as a function of frequency, (f) characterizing said rock formation as a clean rock when said resistance remains constant and said phase is negligible as a function of exciting current frequency, (g) characterizing said rock formation as a low resistivity, high surface area, clay-bearing rock when said resistance remains constant and said phase is a negative value which decreases in magnitude as said exciting current frequency increases, and (h) characterizing said rock formation as a low resistivity, pyrite-bearing rock when said resistance decreases as said exciting current frequency increases and said phase is a negative value which increases in magnitude as said exciting current frequency increases.

It also claims a method for producing a multi-frequency electric log of a subsurface rock formation surrounding a borehole, comprising the steps of: (a) traversing said borehole with a logging tool housing a multi-frequency electric current generator which simultaneously generates a plurality of frequencies, (b) introducing said multi-frequency electric current from said generator into said rock formation through a pair of in-situ current electrodes as said tool traverses the borehole, (c) measuring the resulting voltage in said rock formation through a pair of in-situ voltage electrodes, said voltage representing the reactive component of the electrical impedance of said rock formation, (d) determining the phase and amplitude of said measured voltage at each of the plurality of simultaneous frequencies included in said multi-frequency electric current, (e) determining the resistivity of said rock formation at each of said plurality of simultaneous frequencies included in said multi-frequency electric current, (f) plotting said resistivity, and phase as a function of frequency, (g) characterizing said rock formation as a clean rock when said resistance remains constant and said phase is negligible as a function of exciting current frequency, (h) characterizing said rock formation as a low resistivity, high surface area, clay bearing-rock when said resistance remains constant and said phase is a negative value which decreases in magnitude as said exciting current frequency increases, and (i) characterizing said rock formation as a low resistivity, pyrite-bearing rock when said resistance decreases as said exciting current frequency increases and said phase is a negative value which increases in magnitude as said exciting current frequency increases.

CN11070334A also discusses multi-frequency measurements to reveal more information disclosing a hidden resource prediction method characterized by comprising the following steps: 1) complex impedance measurement: performing complex impedance measurement on an ore body or an oil and gas reservoir and a surrounding rock sample which are obtained from a borehole or a roadway of a detection area in a set frequency range; or in a set frequency range, carrying out in-well complex impedance measurement along a borehole or a roadway of a detection area; 2) characteristic factor extraction: according to the complex impedance measurement result, extracting resistivity and phase information of ore bodies or oil and gas reservoirs in the detection area and surrounding rock samples at different set frequencies, then obtaining impedance phase differences or resistivity ratios of the ore bodies or the oil and gas reservoirs and the surrounding rock samples at multiple set frequencies under the same frequency band, and taking the obtained impedance phase differences or resistivity ratios as electromagnetic characteristic factors; and 3) resource prediction: and predicting the hidden resources of the detection area according to the acquired electromagnetic characteristic factors and a set standard.

WO 2002/50571 is directed to the idea of processing a well logging data with a neural network. It discusses an artificial neural network (ANN) and method of training the ANN for inversion of logging tool signals into well logs of formation parameters. Training is accomplished using properly selected synthetic models (of earth formations). To train the network to process a conductivity log, the logarithm of the synthetic conductivity log that has been generated is fed to the input of the ANN in the form of small windows of data. However, the approach disclosed does not teach the use of frequency dependence in the conductivity (or resistivity) log as well as the ability to predict such frequency dependence.

Another approach to obtain dielectric properties is described in WO 2018/125214 (PEACOCK, Gregg, A. et al.). It discloses tools, systems, and methods for dielectric logging using transient waveforms. Despite these past endeavors, there still exists a need for improved methods of formation evaluation of a formation or formation's surrounding by being able to better detect minerals and other materials such as sulfides (e.g., pyrite) to better estimate the resistivity of fluids in a formation or a formation's surrounding area, particularly, hydrocarbons in a formation.

SUMMARY OF THE INVENTION

A nonlimiting example method of the present disclosure comprises: producing a complex conductivity spectrum for a formation sample over a frequency range of interest, wherein the complex conductivity spectrum is based on a frequency-dependent resistivity for the formation sample; and identifying a physical property of non-ionic conductor grains (c-grains) in the formation sample based on the complex conductivity spectrum and a spectral signature function between a c-grain property and corresponding complex conductivity spectra.

Another nonlimiting example method of the present disclosure comprises: producing a complex conductivity spectrum for a formation sample over a frequency range of interest, wherein the complex conductivity spectrum is based on a frequency-dependent resistivity for the formation sample; and identifying a presence or absence of shale based on the complex conductivity spectrum. The example embodiment may further include identifying a total organic content (TOC) in the shale based on the complex conductivity spectrum.

Yet another nonlimiting example method of the present disclosure comprises: injecting a sinusoidal wave current into a formation sample; measuring a voltage signal response; identifying phase shifts between the sinusoidal wave current and the voltage signal response as the frequency-dependent resistivity; deriving a complex conductivity spectrum from the frequency-dependent resistivity; and physically measuring a physical property of non-ionic conductor grains (c-grains) in the formation sample; and correlating the complex conductivity spectrum to the physical property of the c-grains.

Another nonlimiting example method for performing formation evaluation of a formation and/or formation's surrounding of the present disclosure comprises: (a) providing at least one borehole; (b) measuring a conductivity for the formation's surrounding using a borehole device in a borehole over a plurality of frequencies to produce a complex conductivity spectrum; (c) collecting the complex conductivity spectrum over a detection volume; (d) applying at least one inversion technique to the complex conductivity spectrum to produce an inversion result; and (e) identifying a physical property of non-ionic conductor grains (c-grains) in the detection volume based on the inversion result. The example embodiment may further include combining the inversion result with other formation evaluation information and/or geologic information.

The present disclosure also provides for systems that comprise: a processor, a memory coupled to the processor; and instructions provided to the memory, wherein the instructions are executable by the processor to perform the method of any of the foregoing example embodiments.

DETAILED DESCRIPTION OF THE INVENTION

Before the present compounds, components, compositions, devices, software, hardware, equipment, configurations, schematics, systems, and/or methods are disclosed and described, it is to be understood that unless otherwise indicated this invention is not limited to specific compounds, components, compositions, devices, software, hardware, equipment, configurations, schematics, systems, methods, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an" and "the" include plural referents unless otherwise specified.

Described herein are methods to identify and characterize the abundance and morphology of non-ionic conductor grains, "c-grains", within the formations that are evaluated by formation evaluation (FE) tools. All well logs that are generated as a product of such FE tools are collectively referred to as "FE logs." Some of these logs, such as formation resistivity or apparent density, tend to get modified from their actual value by the presence of c-grains by the application of conventional methods. For example, the concentration and/or volume of c-grains determined by the methods described herein may be used to adjust the apparent density of the formation or formation sample to account for the significantly higher density of c-grains relative to the rock of the formation. Thus, the methods and related systems as disclosed herein are directed to correcting any existing FE logs that can be adversely affected by the presence of c-grains in the detection volume of FE tools, and/or obtaining new FE information that is unavailable by the application of existing FE methods.

Physics-Based Forward Modeling for the Complex Conductivity Associated with Conducting Grains Described herein is a rigorous physics-based forward modeling methodology that can compute the additive contribution of every single non-ionic conductor grain, "c-grain," within an insulating porous medium that is filled with an ionically conducting pore fluid, "p-fluid", to the measured effective complex conductivity. When c-grains are absent, the effective conductivity $\sigma_0$ of the medium typically shows a small amount of frequency dependence if clays or other intrinsically charged minerals are present. These features usually occur at relatively low frequencies, and have a relatively featureless spectrum. A commonly known characterization is in terms of an equivalent constant phase element, and there are other empirical relationships such as Cole-Cole type models that try to tease out this frequency dependence. Existing formation evaluation tools have effective means of isolating such effects to obtain a baseline conductivity $\sigma_0$.

When c-grains with non-ionic conductivities much larger than $\sigma_0$ are present, their contribution to the overall complex conductivity spectrum can be expressed as:

$$\sigma_{eff}(f) = \sigma_0 \left[ 1 + \frac{1}{V_d(f)} \sum_i^{c-grains} V_{eff,i} S_i(f/f_{c,i}) \right].$$

Here, $V_d(f)$ is an effective detection volume of the formation evaluation tool as described earlier, and for each c-grain labeled as i within the detection volume, $V_{eff,i}$ is the effective volume of the conducting component of the c-grain, $f_{c,i}$ is a characteristic frequency associated with the size and morphology of the c-grain, and $S_i$ is a spectral signature associated with the morphology of the c-grain.

This expression provides a sufficiently accurate representation of the effective conductivity spectrum measured by a formation evaluation tool for the purposes of the invention, provided that:

the typical distance between the c-grains are not significantly smaller than their overall size, and characteristic frequencies $f_{c,i}$ of the grains is substantially below the prevailing Debye relaxation frequency $f_D$, given by:

$$f_{c,i} \ll f_D \sim \frac{\sigma_0}{\epsilon},$$

where $\epsilon$ is the effective dielectric constant of the medium.

For most formations of interest for hydrocarbon exploration, these conditions are easily satisfied. The simple additive formula remains accurate to a certain extent, such as for c-grain volume fractions up to 23%.

For example, consider a pyrite c-grain with a framboidal morphology that can be represented as a porous sphere of radius, porosity $\phi$, specific surface area $s_f$, and formation factor $F_f$.

The characteristic frequency of such grains can be expressed as follows:

$$f_{c,i}(a, s_f, C_0) = \frac{\sigma_0}{\pi C_0 a^2} \frac{3}{s_f}, \qquad \text{Equation-1}$$

where the remaining parameter $C_0$ is the differential capacitance of the electric double layer, which depends primarily on the specific mineral, and, to a much lesser extent, to the salts that are dissolved in the p-fluid. A typical number for pyrite is $C_0 \sim 30$ μF/cm$^2$.

The effective volume of pyrite in each grain is given by:

$$V_{eff,i}(a) = \frac{4\pi a^3}{3},$$

and the spectral signature function for pyrite with a framboidal morphology is:

$$S_i^{Framboid}(\tilde{f}) = \frac{3(1 - \alpha(\tilde{f})(F_f + 2))}{1 + 2\alpha(\tilde{f})(F_f - 1)}, \qquad \text{Equation-2}$$

where $$\alpha(\tilde{f}) = \frac{\sqrt{-i\tilde{f}} \cos(\sqrt{-i\tilde{f}}) - \sin(\sqrt{-i\tilde{f}})}{i\tilde{f} \sin(\sqrt{-i\tilde{f}})}.$$

In contrast, for solid c-grains with no internal porosity and aspect ratios near unity, such as solid euhedral pyrite, the spectral signature function is:

$$S_i^{Euhedral}(\tilde{f}) = 3\left(1 - \frac{3}{2(1+i\tilde{f})}\right). \qquad \text{Equation-3}$$

In Equations 2 and 3, the symbol i refers to the unit imaginary number, not the c-grain index.

Therefore, if a prior determination of various morphologies of these c-grains that might be present in the formations of interest have been made, it is possible to make a prior determination of the spectral signature functions associated with them. A multitude of grain morphologies can be handled, and morphology-specific spectral signature functions can be calculated on demand. For more complex morphologies that do not lend themselves to the analytical treatment of the kind above, it is always possible to resort to numerical calculations, or experimental measurements of well-characterized and sorted field samples. An example is provided below.

A well-established and reliable method to determine morphology classes that might be associated with the formations of interest in a particular location is to collect a representative sample set of cores from one or more wells that also include formations of interest, or their analogs, and to subject them to various destructive and/or nondestructive characterization methods. A method commonly established in the prior art is to make a variety of samples suitable for analyses such as optical thin section, polarization microscopy, scanning electron microscopy, secondary ion mass spectrometry, etc. A representative set of samples are chosen and characterized, and used by experts to classify according to size, morphology, and geologic provenance such as depositional environment and diagenetic overprint. While there are dozens of morphological classes documented in the literature, this variety is typically associated with the different environments of deposition and the plethora of possible diagenetic overprint features that are possible somewhere. In a given basin and formation, the depositional and diagenetic environment changes only gradually, therefore within any given formation it is unlikely to find more than one or a few morphological classes in abundance.

While very valuable in terms of linking specific classes to geologically relevant information, this method requires intensive human expert effort, and is generally impractical beyond establishing the morphological class or classes that are present. Our physics-based forward model can use this information to link each morphological class into specific spectral signature functions that can then be fed into a parameter estimation method that uses measured complex conductivity spectra in order to extract abundances and size distributions of each identified class. Some exemplary parameter estimation methods are disclosed below.

Parameter Estimation Methods

In general, parameter estimation can be cast as an optimization problem, where a "forward model" is used to convert a set of hyperparameters that describe the model into an expected measurement. We have forward models that relate the relative abundance of one or more morphological classes to a simulated complex conductivity response $\sigma_{eff}(f)$. In the example provided above, the morphological class of all spherical framboidal pyrite grains that are present can be fully described in terms of the mean c-grain radius a, baseline conductivity $\sigma_0$, and a normalized size distribution p $(V_{eff}/V_{eff}(a))$ such that $$\int_0^\infty dx p(x) = 1.$$

In this particular example, the specific surface area $s_f$, the differential capacitance $C_0$, and the spectral signature function $S(\tilde{f})$ are fully specified in terms of the other hyperparameters and there is no need to estimate them. If there is additional prior information about the type of distribution p(x), this function may also be fully specified and is not included in the parameter space. An exemplary embodiment of this approach may be found in U.S. Patent Application Publication No. US 2020/0018154.

There may be some other situations where the spectral signature function may not be known a priori and may require additional parameterization. It may also be necessary to estimate $s_f$ and $C_0$ if these are not known to the desired accuracy. The optimization problem can then be cast in terms of minimizing an objective function that represents a measure of the misfit between the actual measurement $\hat{\sigma}_{eff}(f)$ and the model response $\sigma_{eff}(f,m)$, where m represents the "model space", that subspace being defined by the set of chosen hyperparameters. An efficient parameterization improves the accuracy of estimates of m.

Typically, the objective function U(m) defined on the model space is some distance measure D defined in the data space, and is called the "data misfit":

$$U(m) = D(\hat{\sigma}_{eff}(f), \sigma_{eff}(f,m)).$$

Any properly defined misfit function is acceptable, but for spectral data, typical distance metrics that are used involve a weighted sum of a frequency-by-frequency difference:

$$D(\hat{\sigma}_{eff}(f), \sigma_{eff}(f, m)) = \sum_{j=1}^{N} A_j W(\|\hat{\sigma}(f_j) - \sigma(f_j, m)\|).$$

Where the weighting function $A_j$ for each frequency $f_j$ are typically chosen based on the variance of the measurement at that frequency. A particular subclass of distance norms use power laws with an exponent p, i.e., $W(x) = x^p$, whose value is chosen based on other statistical properties of the measurement, such as kurtosis. For example, when errors in the measurement are Gaussian-distributed, it is well known that minimizing the 2-norm (p=2) provides the best parameter estimate. For measurement errors with longer-tailed probability distributions, such as the Cauchy distribution, minimizing the 1-norm (p=1) in the equation above may provide a better parameter estimate. Frequency bands with high statistical variance (i.e., low signal-to-noise ratio) are typically assigned lower weights than bands with lower variance (high signal-to-noise ratio). Even if conductivity data is not available over the entire range of frequencies of interest, the inversion can still be performed by setting the weighting function for such frequencies to zero.

The efficient parameterization of the model space may be informed by geologic analysis of a representative rock sample, and fundamental understanding in rock-physics. Alternatively, this efficient parameterization may be achieved using a data-driven approach. This latter approach involves creating a dataset of laboratory measurements from a representative set of rock samples (cores) that contain one or more layers with c-grains in them. These measurements may include $\sigma_{eff}(f)$ in particular, but these measurements may also include other auxiliary properties, such as formation DC resistivity $\hat{\sigma}_{eff}(0)$, formation density $\hat{\rho}$, or any other FE information of interest. We can then use this dataset to train a neural network. This dataset is typically called a training set. One such neural network could be an auto-encoder, which seeks to replicate any function exemplified by a training set, in this case, the underlying function sampled by $\hat{\sigma}(f)$, while only using a small set of abstract parameters; that small set of parameters, typically called latent parameters, may then be substituted for m, and the trained auto-encoder will provide the idealized mapping $\sigma(f,m)$. The auto-encoder serves as a non-linear compression function, achieving the efficient parameterization we desire. After estimating m from new complex conductivity data, by a generic inversion method or direct use of an encoder, these abstract parameters may then be interpreted in light of the paired auxiliary laboratory measurements, e.g. $\hat{\rho}$. In this case, the auto-encoder would also be trained to provide the mapping to the desired formation property, e.g., $\rho(m)$. Preferably, this new complex conductivity data is obtained by running an appropriately configured FE tool, since this data collection method does not involve the costly and laborious recovery of a core sample from the well.

Alternatively, or in addition, a different neural network, set up for classification (rather than compression) could be used. Here, the classes are defined using the auxiliary data. For example, a network could be trained to find the mapping, $\sigma(f) \mapsto \rho$. In this case, $\rho$ functions as part of the efficient parameterization, such that $m = [\rho, \ldots]^T$. The classification network then provides a direct means for estimating m, which is already in geologically interpretable, rather than abstract, terms.

This methodology can therefore allow us to interpret the estimated model parameters to inform other rock properties related to source and reservoir quality, e.g., TOC, along the borehole path. As an additional example, the value extracted for the pore fluid conductivity $\sigma_w$ may also be used to correct traditional resistivity and NMR measurements, logged at the same location of the borehole.

Those skilled in the art are familiar with other ways of choosing an efficient model space based on the complexity of the response and the amount of available data. There are also numerous other well-documented inversion methodologies that are known in the prior art, including, but not limited to Local vs. global optimization, gradient-based, linear vs. non-linear, constrained vs. unconstrained, Occam's method, etc. Any such method that results in an inversion with adequate quality may be used to correct and extract relevant FE information.

Experimental Methods and Systems

Since the experimental measurements described below are typically conducted to generate data for purposes of various inversions, the accuracy of the method affects the uncertainties in the final estimated parameters. Therefore, the phrase "of sufficient accuracy" is meant to imply that bounds on the errors in the measurement yield FE information with sufficient accuracy to be useful for the intended purpose of collecting it.

Described herein are alternate approaches that are more amenable to routine testing of cores, which may allow the analysis of a larger sample set of cores, since the process can be somewhat automated and interpretation-free. This can be important in situations where morphological classes of importance that have yet to be identified are present in cores that were not analyzed with the common intensive method.

This method involves making a sufficiently accurate experimental measurement of the complex conductivity spectrum of intact or simply prepared cores in the sample set over a frequency range of interest, in conjunction with the FE information that we wish to infer from available formation evaluation data.

Figure 1:
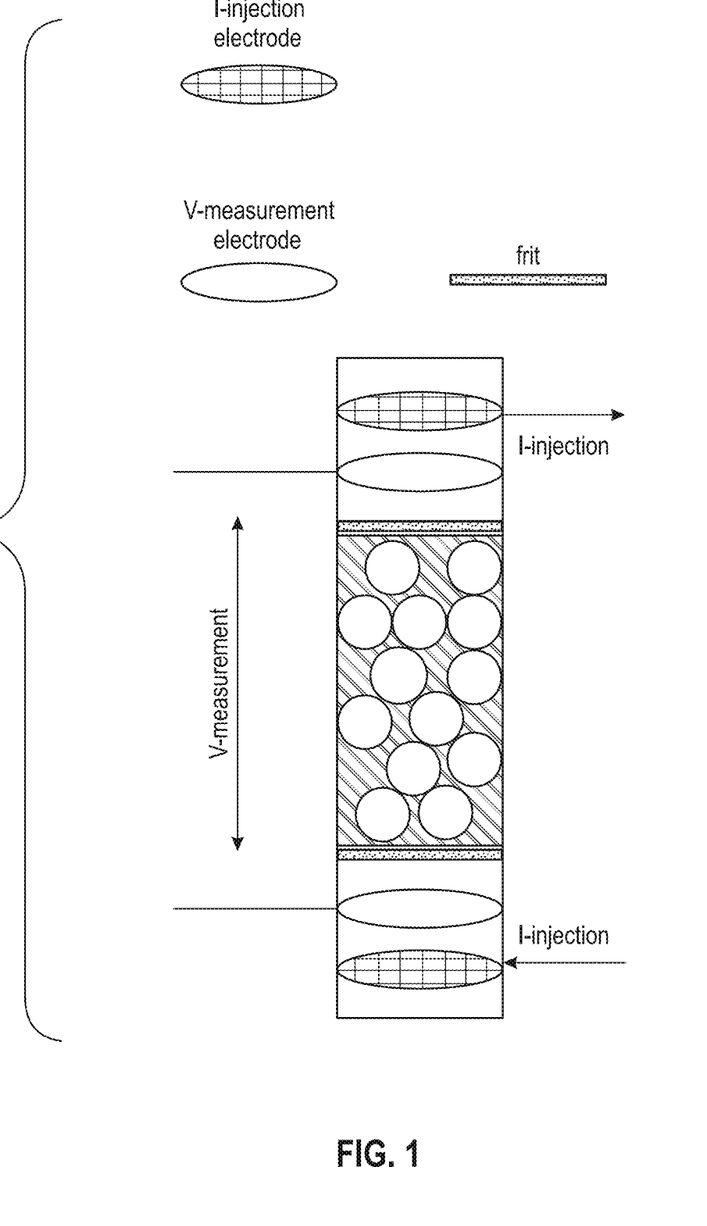
FIG. 1 is an example of a four-probe measurement cell.

The experimental/laboratory methods and systems preferably utilize a custom-designed measurement cell with preferably four electrodes/probes and more preferably with more than four electrodes/probes. FIG. 1 is a graphic view of an exemplary four-probe experimental cell comprising: current electrodes are meshes; voltage electrodes are rings; thin porous frits are used to hold rock core samples in position. In the exemplary measurement cell, the core sample holder is designed as a cylindrical sample holder with a diameter and length consistent with the representative rock core sample. The gap between the core sample and the nearest current electrode is preferably between 0 cm and 100 cm, more preferably between 2 cm and 20 cm and even more preferably approximately 5 cm. The materials of probe electrodes are preferably inert metals such as gold, platinum and stainless steel, and may be made of gold-coated copper. The geometry of the two or more current electrodes are meshes such as square or triangular meshes. The mesh spacing for the two or more current electrodes is designed to guarantee the uniformity of an electric field in core sample while preventing the accumulation of small bubbles, preferably with a spacing between 0.1 mm and 100 mm, more preferably between 1 mm and 10 mm, and even more preferably about 3 mm. The geometry of the two voltage electrodes are ring-shaped and only touching the cylindrical cell on the rim, with minimal metal in the electric current path.

In order to measure broadband complex conductivity spectra for a large set of rock cores and to enable the earlier disclosure of the computational and machine-learning methodology, one or more signal generators are used to generate sinusoidal waves through two or more current electrodes. One or more signal acquisition devices are used to measure the signal response from two or more voltage electrodes. The phase shifts between the injected current and measured voltage are thus obtained in a frequency range preferably from 0.1 Hz to 10 kHz, more preferably from 0.01 Hz to 100 kHz, and even more preferably from 0.001 Hz to 10 MHz.

The signal generator may be any signal generator of sufficient accuracy, with signal generation rates preferably higher than 10 k Samples/s and resolution preferably higher than 8-bit. The waveform of the injected current is measured through a current meter internal to the signal generator or connected to the signal generator.

The signal acquisition device may be a signal acquisition card of sufficient accuracy, with signal acquisition rates preferably higher than 10 k Samples/s and resolution preferably higher than 8-bit. The measured voltage is acquired differentially between two voltage electrodes through one or more signal acquisition devices. Optionally, a pre-amplifier and/or signal filtering device may be placed between the voltage electrode and the signal acquisition device, for example SR560 voltage pre-amplifiers with 100MΩ/25 pF input impedance, to minimize the capacitance coupling.

Figure 2:
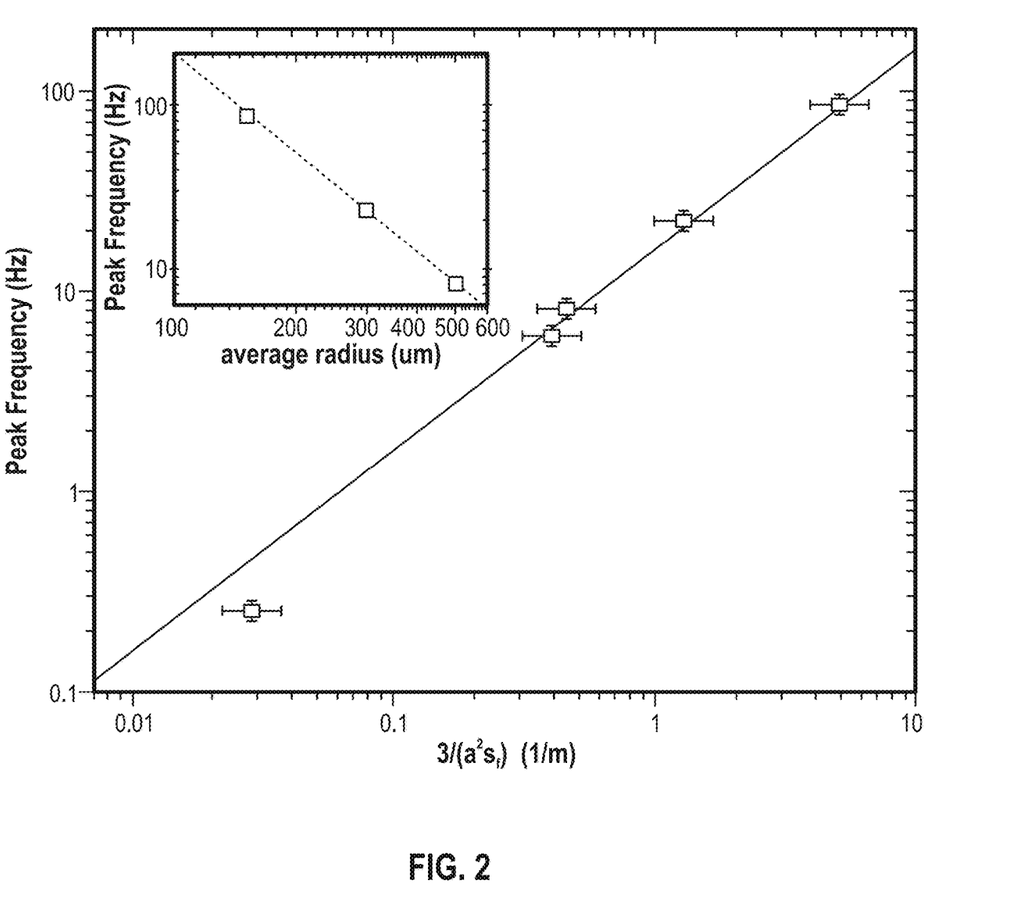
FIG. 2 is a plot of the peak frequency as a function of all data with porous carbon (black squares).

An exemplary experimental measurement data set using the above mentioned experimental/laboratory methods on model conductive materials with framboidal morphology can be found in U.S. Patent Application Nos. US 2018/0149020 and US 2020/0018154. A more detailed analysis of the same dataset leads a more rigorous testing of the scaling from Equation-1 as shown in FIG. 2. With the experimental methodology, it is also possible to quantitatively verify Equation-2 and Equation-3 using materials with framboidal morphology as compared with the solid conductive particles, and an example is provided in FIG. 3.

FIG. 2, more specifically, plots the peak frequency $f_c$ as a function of $$\frac{3}{(a^2 s_f)}$$

for all data with porous carbon (black squares). The line shows the theoretical curve $$f_c \sim \frac{\sigma_m}{\pi C_0} \frac{3}{a^2 s_f}$$

with a surface capacitance $C_0 \sim 3$ µF/cm² for carbon black. For a specific type of porous carbon (Black Pearl 120) with the same porosity parameter $s_f$ and different size a, the peak frequency follows $f \propto 1/a^2$ almost exactly.

Figure 3:
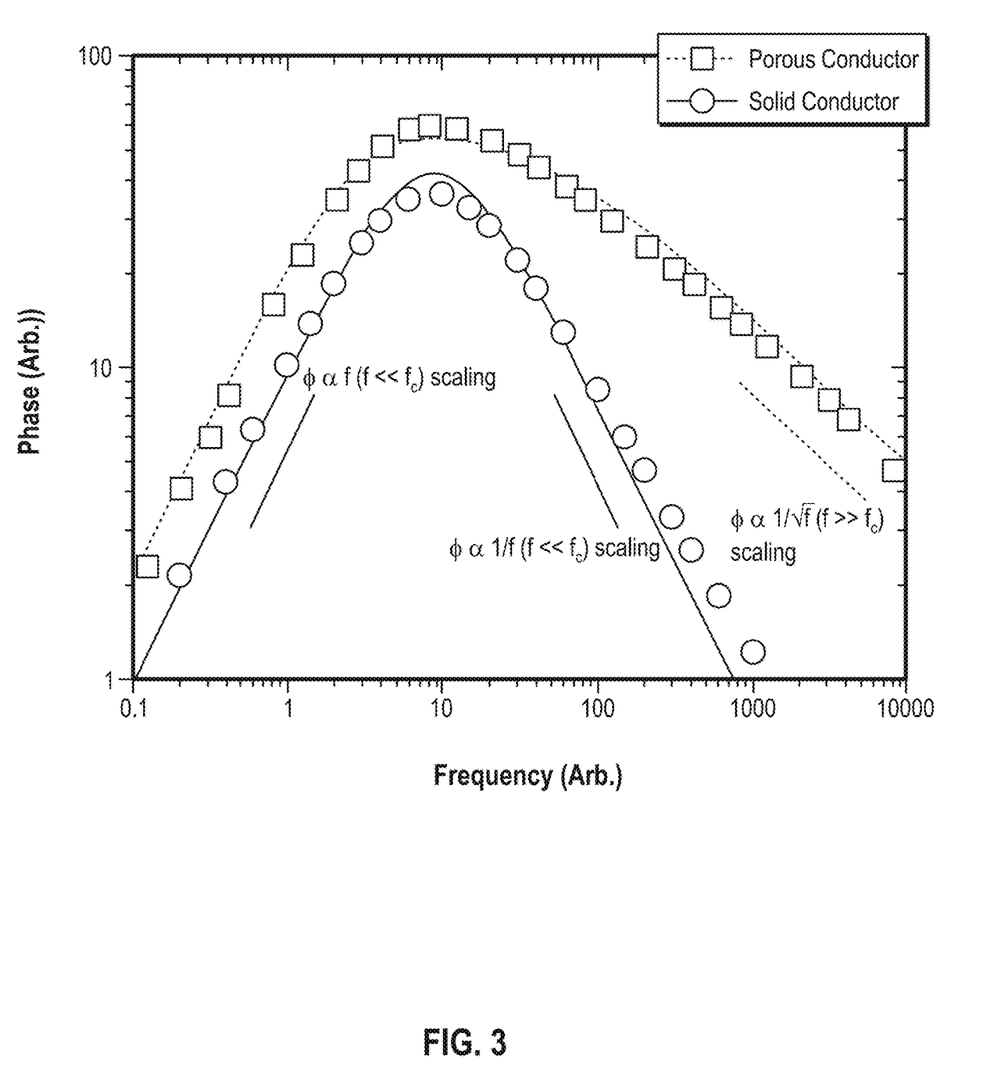
FIG. 3 is a phase vs. frequency plot in log-log scale for a solid conductor and a porous conductor with framboidal morphology.

FIG. 3 is a phase vs. frequency plot in log-log scale for a solid conductor and a porous conductor with framboidal morphology. Squares and circles correspond to experimental data of porous and solid conductors, respectively. The solid curve corresponds to a solid sphere model (Equation-3), whereas the dashed curve corresponds to a framboidal model (Equation-2) with formation factor $F_f \approx 3$. FIG. 3 also includes guides for scalings $\phi \propto f(f<<f_c)$, $\phi \propto 1/f(f>>f_c)$, and $\phi \propto 1/\sqrt{f}$, which only happens in porous conductors at high frequency ($f>>f_c$).

In addition to the above-mentioned experimental methodology for measuring broadband complex conductivity spectra of core samples, other auxiliary formation properties such as density, porosity, permeability, p-wave velocity can be readily acquired using standard lab/commercial testing protocols. For example, the porosity of a rock core can be measured through neutron porosity measurement. As another example, the porosity and the density of a rock core can be measured with the weight of an evaporated and dried core, the weight of the same core sample fully saturated with water, and the volume measurement with the water saturated core. As another example, the permeability of a rock core can be estimated with T2 relaxation measurements by nuclear magnetic resonance (NMR) of the core sample. As yet another example, the p-wave velocity of a rock core can be measured with a standard lab ultrasound technique.

The morphology information of metallic inclusions in core samples can be readily obtained using various experimental methods and systems, such as crushing and/or dissolving the rock matrix using certain solvents. As an example, for pyrite-bearing organic-rich sapropel core samples, pyrite samples can be extracted with improved pyrite concentration by using a sieving process (90 µm) in seawater to concentrate minerals and large aggregates, as in similar sedimentary environments the presence of pyrites is often associated with forams that are often larger than 30 µm. As another example, a customized magnetic gradient concentrator can be used to extract and concentrate materials containing pyrites as pyrites are weakly paramagnetic materials. In this scenario, several cubic neodymium permanent magnets (1.2 cm cubes) were placed at the surface of a flow system, and the dispersed grains containing paramagnetic pyrites were attracted to the high magnetic gradient zones (corners of the cubic magnet), and then extracted and concentrated by careful rinsing and gravitational separation.

Figure 4:
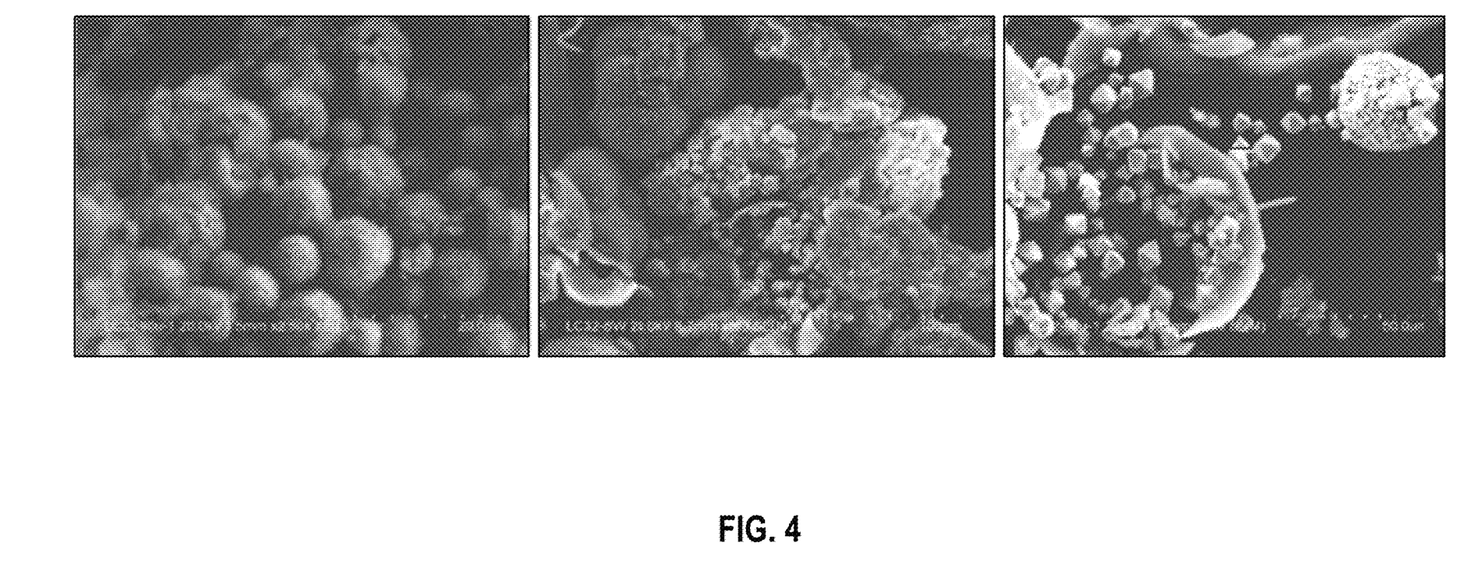
FIG. 4 shows SEM images of extracted pyrites from sapropel core samples with euhedral and framboidal morphologies.
Figure 5:
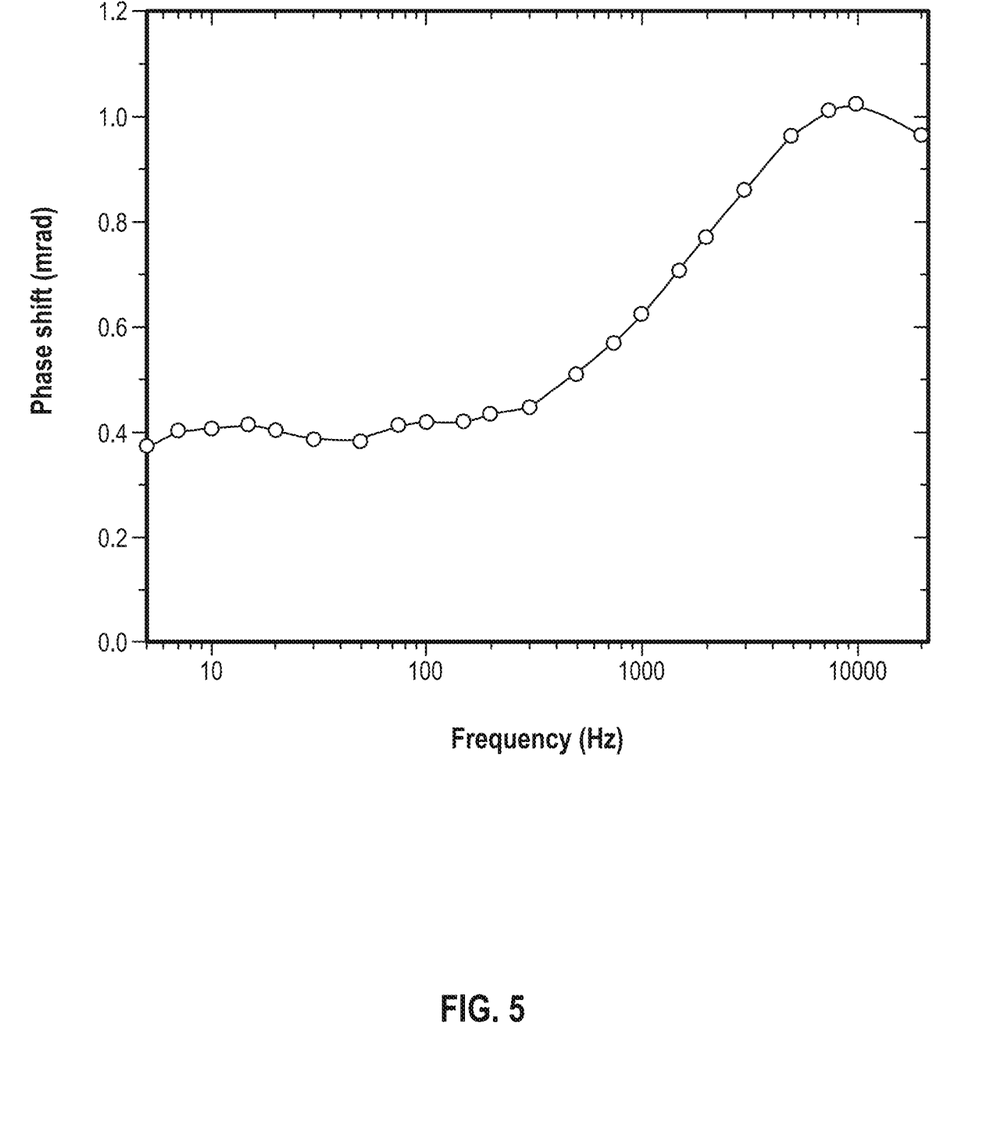
FIG. 5 represents a broadband complex conductivity spectra with framboidal pyrites extracted from a sapropel core sample.

After extracting the metallic inclusions in the rock sample, one can then use different experimental tools to analyze the morphology, volume fraction and size distribution of specific metallic inclusions. FIG. 4 shows SEM images of extracted pyrites from sapropel core samples with euhedral and framboidal morphologies. FIG. 5 represents a broadband complex conductivity spectra with framboidal pyrites extracted from a sapropel core sample (same sample of the middle figure in FIG. 4). For example, the extracted metallic inclusions can be analyzed with Scanning Electron Microscopy (SEM) to measure size distribution and morphology of the extracted metallic inclusions (see examples in FIG. 4 for euhedral and framboidal pyrite morphology), with energy-dispersive X-ray spectroscopy (EDS) to confirm elemental composition, with x-ray photoelectron spectroscopy (XPS) to measure elemental composition and electronic states, with Brunauer-Emmett-Teller (BET) technique to measure specific surface areas through physical adsorption of gas molecules. In addition to these characterization methods, broadband complex conductivity spectra as disclosed herein can also be measured with the extracted metallic inclusion samples to provide a complete dataset to enable efficient parameterization as disclosed earlier, and an example is shown in FIG. 5.

Based on broadband complex conductivity well log data, one can use established spectral signature functions to infer morphology information of metallic inclusions. The reservoir quality can then be obtained based on previously established relationships between morphology and reservoir quality.

The methods and systems disclosed above can be combined in various ways to generate improved estimates of FE information, which in turn is used for a multitude of purposes, including, but not limited to.
  i. improving the estimation of the resistivity of fluids in the formation,
  ii. resource characterization,
  iii. exploration targets elsewhere within the same basin, or in other analog basins, and
  iv. making operational decisions such as well placement and planning, geosteering, etc.

Figure 6:
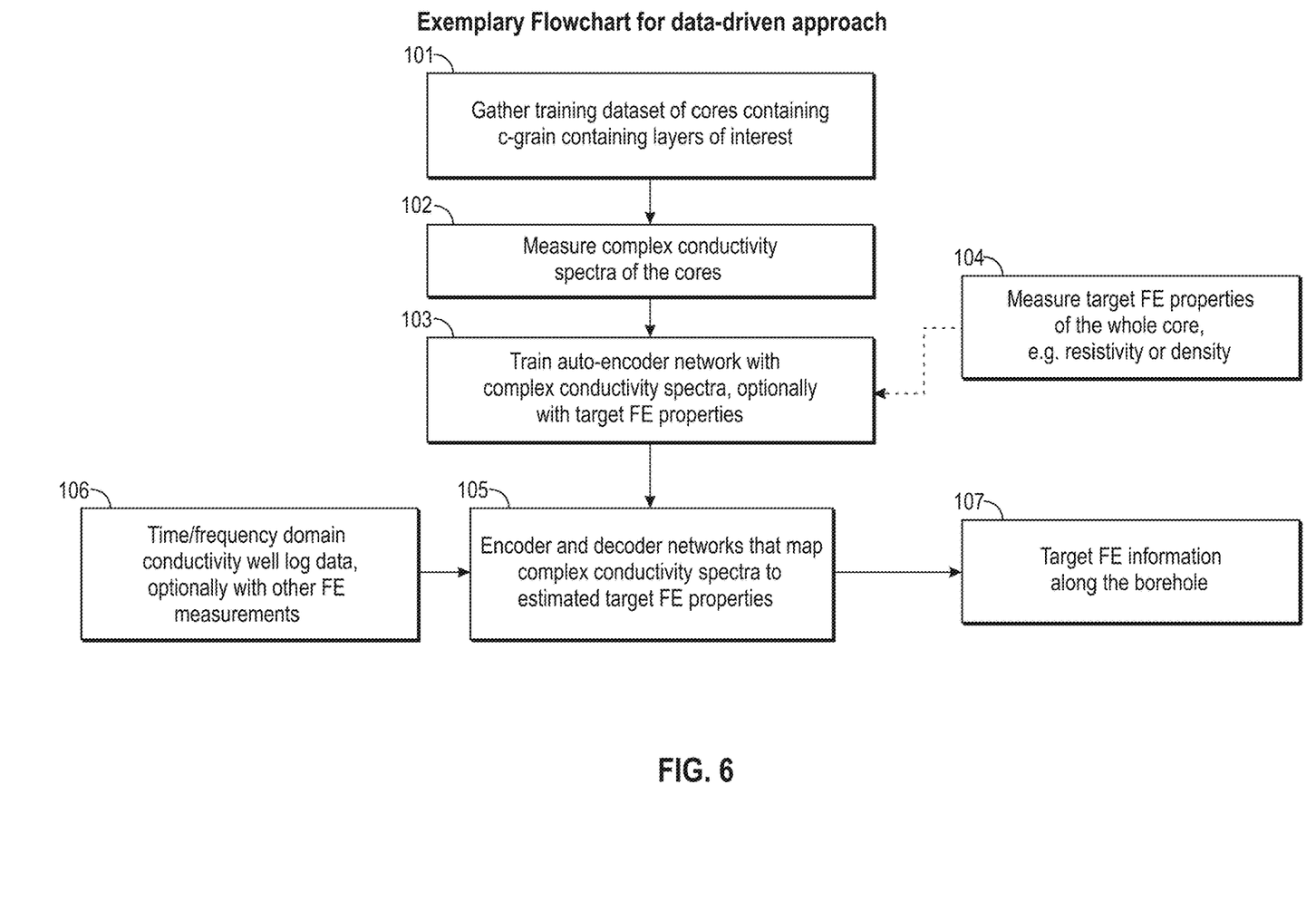
FIG. 6 is a flowchart of a data-driven approach of a method of one embodiment of the invention.

An exemplary embodiment of a data-driven approach is outlined in FIG. 6. The process starts with identifying or obtaining suitable core samples (101). Then, complex conductivity spectra are measured with one or more experimental methods (102). This data is fed into a neural network, here shown as an auto-encoder (103) that can optionally be also encoded with auxiliary variables that correspond to target FE properties (105). The training process results in encoders and decoders (105) then can be used to transform conductivity and optionally other FE logs (106) into improved estimates of target FE information (107).

Figure 7:
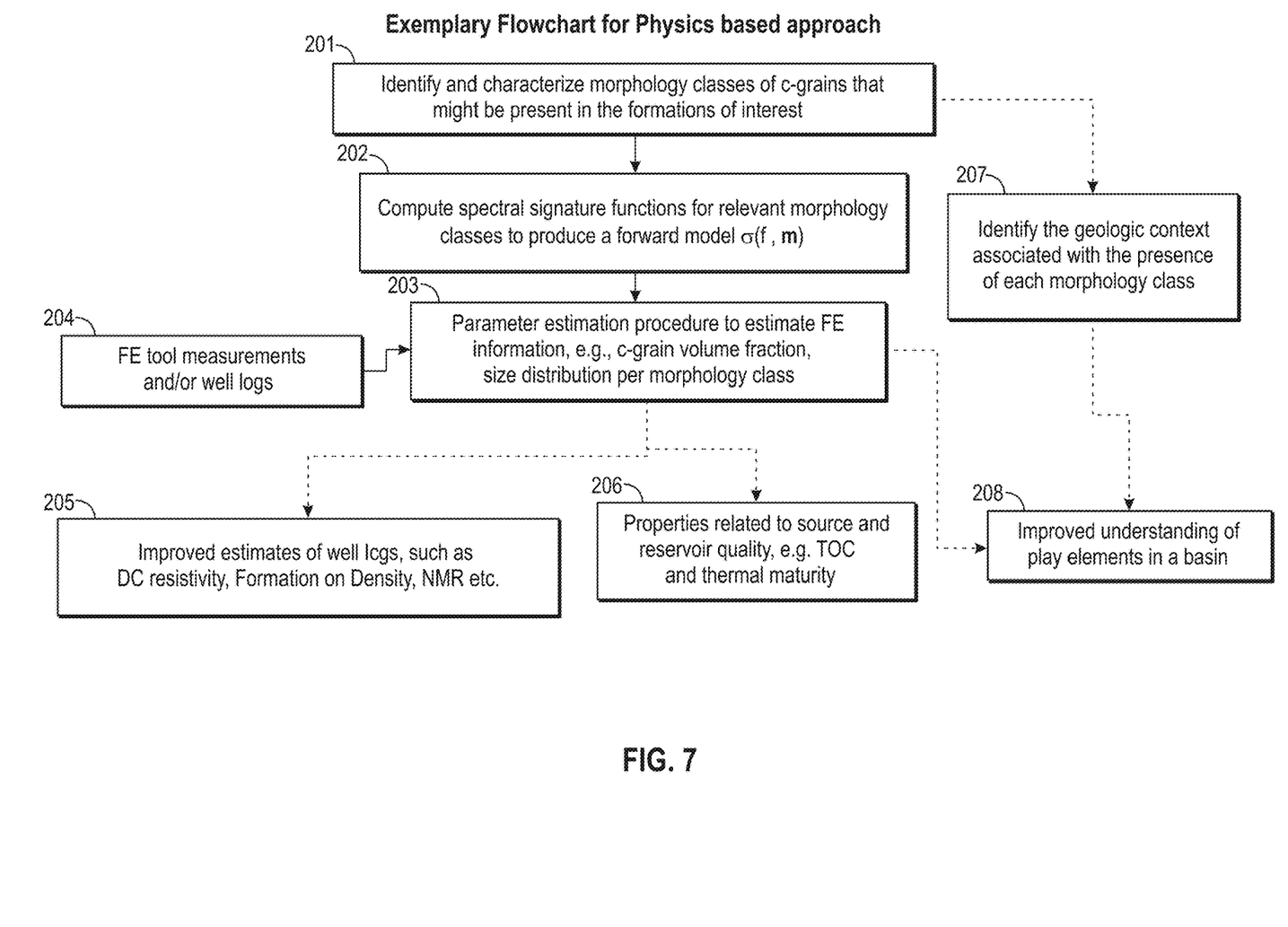
FIG. 7 is a flowchart of a physics-based approach of a method of another embodiment of the invention.

An exemplary embodiment of a physics-based approach is outlined in FIG. 7. The process starts with identifying and characterizing morphology classes of c-grains that might be present in the formations of interest (201). Then, a physics-based forward model is used to compute the spectral signature functions and other hyperparameters that are needed to describe the complex conductivity response of a representative element within the detection volume of the FE tool (202). This forward model is then used, preferably in combination with a forward simulation that maps this information to the signal measured by the FE tool, in a parameter estimation procedure (203), which can utilize direct measurements of FE tools and/or processed well logs (204). The parameters obtained constitute a new set of well logs that were previously unknown to those skilled in FE. If desired, these new parameters can be used to obtain improved estimates of well logs, in some cases obviating the necessity of running other tools that would otherwise be required (205). Additionally, the parameter estimation procedure may yield FE information that is not directly available from existing well logs, such as TOC (206). Furthermore, if the morphology classes identified in step (201) relate to the geologic context of the presence of such morphologies, such as environment of deposition and possible diagenetic overprint (207), this information can be used in conjunction with the information obtained in step (203) and other prior information to obtain an improved understanding of play elements in a hydrocarbon basin (208).

Borehole logging of resistivity can be performed in either the time or frequency domain. U.S. Pat. No. 4,849,699 discloses a pulsed induction logging tool that should be capable of performing such measurements, possibly with some modifications. When performed in the time domain, the frequency content of the measurement should be such that frequencies ranging from 0.01 Hz to 1.1 GHz are sampled or alternatively from 10 Hz to 1.1 GHz or alternatively from 100 Hz to 500 MHz or alternatively from 1 Khz to 100 KHz. When performed in frequency domain, the measurement should be such that frequencies ranging from 0.01 Hz to 1.1 GHz are sampled or alternatively from 10 Hz to 1.1 GHz or alternatively from 100 Hz to 500 MHz or alternatively from 1 KHz to 100 KHz. For frequency domain measurements at least 4 different frequency bands should be sampled, preferably at least 10 frequency bands and more preferably at least 100 frequency bands and even more preferably 1,000 frequency bands. When laboratory measurements of core samples are used for calibration it is preferable that the measurements span a range from 0.1 Hz to 10 kHz, more preferably from 0.01 Hz to 100 kHz, and even more preferably from 0.001 Hz to 10 MHz. Alternatively the lab measurements can span a frequency range from 0.01 Hz to 1.1 GHz are sampled or from 10 Hz to 1.1 GHz or from 100 Hz to 500 Mhz or from 1 kHz to 100 kHz.

Those skilled in the art will recognize that a conductivity is the reciprocal of the resistivity and that a frequency dependent conductivity measurement that records both amplitude and phase is the equivalent of a complex conductivity measurement.

Physical properties of c-grains are taken to be quantities such as abundance (or concentration), and/or morphology, and/or size distribution and/or average size, and/or differential capacitance, and/or specific surface area. Generally, any physical property that alters the contribution of a particular c-grain to the complex conductivity can in principle be estimated.

Various aspects of the systems and methods described herein utilize computer systems. Such systems and methods can include a non-transitory, computer-readable medium containing instructions that, when implemented, cause one or more processors to carry out the methods described herein.

"Computer-readable medium" or "non-transitory, computer-readable medium," as used herein, refers to any non-transitory storage and/or transmission medium that participates in providing instructions to a processor for execution. Such a medium may include, but is not limited to, non-volatile media and volatile media. Non-volatile media includes, for example, NVRAM, or magnetic or optical disks. Volatile media includes dynamic memory, such as main memory. Common forms of computer-readable media include, for example, a floppy disk, a flexible disk, a hard disk, an array of hard disks, a magnetic tape, or any other magnetic medium, magneto-optical medium, a CD-ROM, a holographic medium, any other optical medium, a RAM, a PROM, and EPROM, a FLASH-EPROM, a solid state medium like a memory card, any other memory chip or cartridge, or any other tangible medium from which a computer can read data or instructions. When the computer-readable media is configured as a database, it is to be understood that the database may be any type of database, such as relational, hierarchical, object-oriented, and/or the like. Accordingly, exemplary embodiments of the present systems and methods may be considered to include a tangible storage medium or tangible distribution medium and prior art-recognized equivalents and successor media, in which the software implementations embodying the present techniques are stored.

The methods described herein can, and in many embodiments must, be performed using computing devices or processor-based devices that include a processor; a memory coupled to the processor; and instructions provided to the memory, wherein the instructions are executable by the processor to perform the methods described herein. The instructions can be a portion of code on a non-transitory, computer-readable medium. Any suitable processor-based device may be utilized for implementing all or a portion of embodiments of the present techniques, including without the limitation of personal computers, networks, laptop computers, computer workstations, mobile devices, multi-processor servers or workstations with (or without) shared memory, high-performance computers, and the like. Moreover, embodiments may be implemented on application-specific integrated circuits (ASICs) or very large scale integrated (VLSI) circuits.

For example, a system may comprise a processor; a memory coupled to the processor; and instructions provided to the memory, wherein the instructions are executable by the processor to perform a method that comprises: producing a complex conductivity spectrum for a formation sample over a frequency range of interest, wherein the complex conductivity spectrum is based on a frequency-dependent resistivity for the formation sample, and identifying a physical property of non-ionic conductor grains (c-grains) in the formation sample based on the complex conductivity spectrum and a spectral signature function between a c-grain property and corresponding complex conductivity spectra.

In another example, a system may comprise a processor; a memory coupled to the processor; and instructions provided to the memory, wherein the instructions are executable by the processor to perform a method that comprises: producing a complex conductivity spectrum for a formation sample over a frequency range of interest, wherein the complex conductivity spectrum is based on a frequency-dependent resistivity for the formation sample; and identifying a presence or absence of shale based on the complex conductivity spectrum.

In yet another example, a system may comprise a processor; a memory coupled to the processor; and instructions provided to the memory, wherein the instructions are executable by the processor to perform a method that comprises: injecting a sinusoidal wave current into a formation sample; measuring a voltage signal response; identifying phase shifts between the sinusoidal wave current and the voltage signal response as the frequency-dependent resistivity; deriving a complex conductivity spectrum from the frequency-dependent resistivity; physically measuring a physical property of non-ionic conductor grains (c-grains) in the formation sample; and correlating the complex conductivity spectrum to the physical property of the c-grains.

In yet another example, a system may comprise a processor; a memory coupled to the processor; and instructions provided to the memory, wherein the instructions are executable by the processor to perform a method for performing formation evaluation of a formation and/or formation's surrounding that comprises: (a) providing at least one borehole; (b) measuring a conductivity for the formation's surrounding using a borehole device in a borehole over a plurality of frequencies to produce a complex conductivity spectrum; (c) collecting the complex conductivity spectrum over a detection volume; (d) applying at least one inversion technique to the complex conductivity spectrum to produce an inversion result; and (e) identifying a physical property of non-ionic conductor grains (c-grains) in the detection volume based on the inversion result.

EXAMPLE EMBODIMENTS

A first nonlimiting example embodiment of the present disclosure is a method comprising: producing a complex conductivity spectrum for a formation sample over a frequency range of interest, wherein the complex conductivity spectrum is based on a frequency-dependent resistivity for the formation sample; and identifying a physical property of non-ionic conductor grains (c-grains) in the formation sample based on the complex conductivity spectrum and a spectral signature function between a c-grain property and corresponding complex conductivity spectra. The first nonlimiting example embodiment may further include one or more of: Element 1: the method further comprising: collecting the complex conductivity spectrum by performing steps comprising: injecting a sinusoidal wave current into the formation sample; measuring a voltage signal response; and identifying phase shifts between the sinusoidal wave current and the voltage signal response as the frequency-dependent resistivity; Element 2: wherein the physical property is selected from the group consisting of: a concentration of the c-grains, a morphology of the c-grains, a size distribution of the c-grains, an average size of the c-grains, a differential capacitance of the c-grains, a specific surface area of the c-grains, and any combination thereof; Element 3: the method further comprising: logging a borehole of a formation to measure the frequency-dependent resistivity for at least a portion of the formation; Element 4: wherein the formation sample is a core sample; Element 5: wherein the frequency-dependent resistivity comprises amplitude frequency-dependent resistivity information and phase frequency-dependent resistivity information; Element 6: wherein the frequency-dependent resistivity is measured over a broadband; Element 7: wherein the frequency-dependent resistivity is assessed for at least 100 discrete frequencies; Element 8: wherein the frequency-dependent resistivity comprises a frequency content over frequencies within 0.01 Hz to 1.1 GHz; Element 9: wherein the frequency-dependent resistivity comprises a frequency content over frequencies within 0.01 Hz to 1.1 GHz with at least 4 different frequency bands; Element 10: the method further comprising: adjusting the apparent density of the formation sample based on the physical property; Element 11: wherein the spectral signature function applies an inversion algorithm to the complex conductivity spectrum; Element 12: Element 11 and wherein the inversion algorithm is calibrated with data from core samples; Element 13: Element 11 and wherein the inversion algorithm is calibrated with a physics-based model; Element 14: Element 11 and wherein identifying the physical property of the c-grains uses a machine-learning algorithm; Element 15: Element 14 and wherein data from core samples is used to train the machine-learning algorithm; and Element 16: Element 14 and wherein a physics-based model is used to train the machine-learning algorithm. Examples of combinations include, but are not limited to, Element 1 in combination with one or more of Elements 2-16; Element 2 in combination with one or more of Elements 3-16; Element 3 in combination with one or more of Elements 4-16; Element 4 in combination with one or more of Elements 5-16; Element 5 in combination with one or more of Elements 6-16; Element 6 and/or 7 in combination with one or more of Elements 8-16; Element 8 or 9 in combination with one or more of Elements 10-16; Element 10 in combination with one or more of Elements 11-16; Element 11 in combination with two or more of Elements 12-14; and Elements 11 and 14 in combination with Elements 15 and 16.

A second nonlimiting example embodiment of the present disclosure is a method comprising: producing a complex conductivity spectrum for a formation sample over a frequency range of interest, wherein the complex conductivity spectrum is based on a frequency-dependent resistivity for the formation sample; and identifying a presence or absence of shale based on the complex conductivity spectrum. The second nonlimiting example embodiment may further include identifying a total organic content (TOC) in the shale based on the complex conductivity spectrum.

A third nonlimiting example embodiment of the present disclosure is a method comprising: injecting a sinusoidal wave current into a formation sample: measuring a voltage signal response; identifying phase shifts between the sinusoidal wave current and the voltage signal response as the frequency-dependent resistivity; deriving a complex conductivity spectrum from the frequency-dependent resistivity; and physically measuring a physical property of non-ionic conductor grains (c-grains) in the formation sample; and correlating the complex conductivity spectrum to the physical property of the c-grains.

A fourth nonlimiting example embodiment of the present disclosure is a method for performing formation evaluation of a formation and/or formation's surrounding, the method comprising: (a) providing at least one borehole; (b) measuring a conductivity for the formation's surrounding using a borehole device in a borehole over a plurality of frequencies to produce a complex conductivity spectrum; (c) collecting the complex conductivity spectrum over a detection volume; (d) applying at least one inversion technique to the complex conductivity spectrum to produce an inversion result, and (e) identifying a physical property of non-ionic conductor grains (c-grains) in the detection volume based on the inversion result. The fourth nonlimiting example embodiment may further include combining the inversion result with other formation evaluation information and/or geologic information. In addition, the fourth nonlimiting example may further include one or more of: (f) improving the estimation of the resistivity of fluids in the formation; (g) resource characterization; (h) detecting exploration targets elsewhere within the same basin or in another analog basin; and (i) using the inversion result to make well placement and/or geosteering decisions.

Additional nonlimiting example embodiments include systems that comprise: a processor; a memory coupled to the processor; and instructions provided to the memory, wherein the instructions are executable by the processor to perform the method of any of the first, second, third, or fourth nonlimiting example embodiments.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the invention, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All priority documents are herein fully incorporated by reference for all jurisdictions in which such incorporation is permitted and to the extent such disclosure is consistent with the description of the present invention. Further, all documents and references cited herein, including testing procedures, publications, patents, journal articles, etc. are herein fully incorporated by reference for all jurisdictions in which such incorporation is permitted and to the extent such disclosure is consistent with the description of the present invention.

While the invention has been described with respect to a number of embodiments and examples, those skilled in the art, having the benefit of this disclosure, will appreciate that other embodiments can be devised which do not depart from the scope and spirit of the invention as disclosed herein.

What is claimed:

1. A method comprising:
    producing a complex conductivity spectrum for a formation sample over a frequency range of interest, wherein the complex conductivity spectrum is based on a frequency-dependent resistivity for the formation sample; and
    identifying a physical property of non-ionic conductor grains (c-grains) in the formation sample based on the complex conductivity spectrum and a spectral signature function between a c-grain property and corresponding complex conductivity spectra; wherein the c-grains are non-ionically conducting sulfides and/or pyrite.

2. The method of claim 1 further comprising:
    collecting the complex conductivity spectrum by performing steps comprising:
        injecting a sinusoidal wave current into the formation sample;

measuring a voltage signal response; and
identifying phase shifts between the sinusoidal wave current and the voltage signal response as the frequency-dependent resistivity.

3. The method of claim 1, wherein the physical property is selected from the group consisting of: a concentration of the c-grains, a morphology of the c-grains, a size distribution of the c-grains, an average size of the c-grains, a differential capacitance of the c-grains, a specific surface area of the c-grains and any combination thereof.

4. The method of claim 1 further comprising:
logging a borehole of a formation to measure the frequency-dependent resistivity for at least a portion of the formation.

5. The method of claim 1, wherein the formation sample is a core sample.

6. The method of claim 1, wherein the frequency-dependent resistivity comprises amplitude frequency-dependent resistivity information and phase frequency-dependent resistivity information.

7. The method of claim 1, wherein the frequency-dependent resistivity is measure over a broadband.

8. The method of claim 1, wherein the frequency-dependent resistivity is assessed for at least 100 discrete frequencies.

9. The method of claim 1, wherein the frequency-dependent resistivity comprises a frequency content over frequencies within 0.01 Hz to 1.1 GHz.

10. The method of claim 1, wherein the frequency-dependent resistivity comprises a frequency content over frequencies within 0.01 Hz to 1.1 GHz with at least 4 different frequency bands.

11. The method of claim 1 further comprising:
adjusting the apparent density of the formation sample based on the physical property.

12. The method of claim 1, wherein the spectral signature function applies an inversion algorithm to the complex conductivity spectrum.

13. The method of claim 12, wherein the inversion algorithm is calibrated with data from core samples.

14. The method of claim 12, wherein the inversion algorithm is calibrated with a physics-based model.

15. The method of claim 12, wherein identifying a physical property of the c-grains uses a machine-learning algorithm.

16. The method of claim 15, wherein data from core samples is used to train the machine-learning algorithm.

17. The method of claim 15, wherein a physics-based model is used to train the machine-learning algorithm.

18. A system comprising:
a processor;
a memory coupled to the processor; and
instructions provided to the memory, wherein the instructions are executable by the processor to perform the method of claim 1.

19. A method comprising:
injecting a sinusoidal wave current into a formation sample;
measuring a voltage signal response;
identifying phase shifts between the sinusoidal wave current and the voltage signal response as the frequency-dependent resistivity;
deriving a complex conductivity spectrum from the frequency-dependent resistivity; and
physically measuring a physical property of non-ionic conductor grains (c-grains) in the formation sample; wherein the c-grains are non-ionically conducting sulfides and/or pyrite; and
correlating the complex conductivity spectrum to the physical property of the c-grains.

20. A method for performing formation evaluation of a formation and/or formation's surrounding, the method comprising:
(a) providing at least one borehole;
(b) measuring a conductivity for the formation's surrounding using a borehole device in a borehole over a plurality of frequencies to produce a complex conductivity spectrum;
(c) collecting the complex conductivity spectrum over a detection volume;
(d) applying at least one inversion technique to the complex conductivity spectrum to produce an inversion result; and
(e) identifying a physical property of non-ionic conductor grains (c-grains) in the detection volume based on the inversion result; wherein the c-grains are non-ionically conducting sulfides and/or pyrite.

21. The method of claim 20 further comprising:
combining the inversion result with other formation evaluation information and/or geologic information.

22. The method of claim 20 further comprising one or more of:
(f) improving the estimation of the resistivity of fluids in the formation;
(g) resource characterization;
(h) detecting exploration targets elsewhere within the same basin or in another analog basin; and
(i) using the inversion result to make well placement and/or geosteering decisions.

* * * * *